United States Patent [19]

Prystowsky et al.

[11] Patent Number: 4,554,922
[45] Date of Patent: Nov. 26, 1985

[54] METHOD OF INHIBITING CARDIAC ARRHYTHMIAS

[76] Inventors: Eric N. Prystowsky, 9013 Sweetbay Ct.; Douglas P. Zipes, 2113 Brewster Rd., both of Indianapolis, Ind. 46260

[21] Appl. No.: 429,827

[22] Filed: Sep. 30, 1982

[51] Int. Cl.⁴ ............................................. A61N 1/36
[52] U.S. Cl. .............................................. 128/419 PG
[58] Field of Search ................... 128/419 PG, 419 D

[56] References Cited

U.S. PATENT DOCUMENTS

| | | | |
|---|---|---|---|
| 3,662,759 | 5/1972 | Dabolt | 128/419 PG |
| 3,693,627 | 9/1972 | Berkovits | 128/419 PG |
| 3,937,226 | 2/1976 | Funke | 128/419 PG |
| 3,939,844 | 2/1976 | Pequignot | 128/419 PG |

OTHER PUBLICATIONS

"Interaction of Sequential Stimuli Applied During the Relative Refractory Period in Relation to Determination of Fibrillation Threshold in the Canine Ventricle", Circulation Research, vol. 37, Nov. 1975, Juan Tamargo, Bruce Moe, and Gordon K. Moe.

Primary Examiner—William E. Kamm
Attorney, Agent, or Firm—Barnes & Thornburg

[57] ABSTRACT

Inhibition of cardiac arrhythmias such as tachycardia and fibrillation is achieved by determining a refractory period after a selected heartbeat during which a stimulus applied to the heart will not propagate a heart response, determining a time within the refractory period after the selected heartbeat for the application of one or more electrical pulses to the heart to inhibit arrhythmic beats, determining a voltage of the electrical pulse as a function of the time which will inhibit the arrhythmic beats, and applying the electrical pulse to an area of the heart at the determined time to inhibit the arrhythmic beats. A plurality of electrical pulses may be employed having various voltage levels related to the times at which they are applied during the refractory period. One or more electrical pulses may be applied after the refractory period, each having a voltage providing a current less than a threshold current which would propagate a heart response.

12 Claims, 8 Drawing Figures (VENTRICULAR INHIBITION)

I = 1.4 mA

I = 3.6 mA

I = 5.4 mA

I = 6.2 mA $S_C S_2 (t_c) = 30$ msec $S_C S_2 (t_c) = 80$ msec $S_C S_2 (t_c) = 130$ msec $S_C S_2 (t_c) = 150$ msec I = 1.6 mA I = 3.8 mA I = 5.6 mA I = 6.4 mA

METHOD OF INHIBITING CARDIAC ARRHYTHMIAS

The invention relates to pacemakers, and more particularly to a method of inhibiting a variety of cardiac arrhythmias, including atrial and ventricular tachycardia and fibrillation.

A cardiac arrhythmia is an alteration in the rhythm of the heartbeat. There are a variety of cardiac arrhythmias. One such arrhythmia is atrial or ventricular fibrillation. Fibrillation is an uncoordinated contraction and relaxation of the individual fibers of the heart which produces no blood flow and, when present in the ventricles, results in death unless corrective measures are applied within minutes of onset. Generally speaking, fibrillation can originate in any area of the heart. Heretofore, efforts have been directed toward the treatment of arrhythmias, including fibrillation, after they occur. One conventional treatment calls for the application of an electric shock of sufficient voltage or current strength to depolarize the myocardium, e.g., by way of a pair of electrodes ("paddles") across the chest of the patient. Heretofore, efforts to inhibit arrhythmias before they occur have been limited to the use of drugs. No efforts have been made to inhibit the arrhythmias using stimulators or other devices.

It is known that an electrical stimulus delivered to the heart during its refractory period can prevent a propagated response to a subsequent stimulus delivered after the refractory period. In particular, if the stimuli are electrical pulses and the subsequent electrical pulse has a predetermined threshold voltage for initiating a response, it is known that the application of an electrical pulse having a subthreshold voltage during the refractory period will prevent a propagated response. This knowledge was first demonstrated by A. N. Drury and W. S. Love. (See A. N. Drury and W. S. Love, "Supposed Lengthening of the Absolute Refractory Period of Frog's Ventricle Muscle by Veratine", *Heart*, Vol. 13, pp. 77-85 (1926) and W. S. Love, "Effect of Quinidine and Strophanthin Upon the Refractory Period of the Tortoise Ventricle", *Heart*, Vol. 13, pp. 87-93 (1926).) Their demonstration and disclosure were subsequently summarized and applied by Juan Tamargo, Bruce Moe, and Gordon K. Moe in an article entitled "Interaction of Sequential Stimuli Applied During the Relative Refractory Period in Relation to Determination of Fibrillation Threshold in the Canine Ventricle", *Circulation Research*, Vol. 37, November 1975. The Drury and Love demonstration was applied by Tamargo, Moe, and Moe in a method of determining the threshold at which fibrillation occurs.

According to the present invention, one or more electrical stimulus(i) is (are) applied to the heart at a predetermined time after every or only selected heartbeats to inhibit arrhythmias. The predetermined time is selected within the refractory period and the voltage of the electrical stimulus is determined as a function of the predetermined time. Preferably, the electrical stimulus is applied within a relatively short period of time after the selected heartbeat.

Further according to the present invention, single or multiple electrodes are positioned at single or multiple areas of the heart and the electrical stimulus(i) applied simultaneously to each electrode to inhibit the arrhythmias regardless of where they may originate in the heart. In a preferred embodiment, the multiple electrodes are equally spaced apart at a predetermined distance.

In accordance with the method of the present invention, multiple electrical stimuli may be applied at various times within the refractory period. Each electrical stimulus has a voltage which is determined in relationship to the time at which it is applied to the heart. The voltage of the electrical stimuli varies in an inverse relationship with respect to the time period between the heartbeat and the time when the electrical stimulus is applied to the heart.

It is thus an object of the present invention to inhibit arrhythmias and prevent their occurrence as opposed to treating the arrhythmias after their occurrence.

Other objects and advantages of the present invention will be apparent from the following description of the accompanying drawings which illustrate and explain the invention and also show a preferred embodiment exemplifying the best mode of carrying out the invention as presently perceived. In such drawings.

It has previously been shown that by applying an electrical stimulus to a heart during the refractory period after a heartbeat, a response which would be propagated by a subsequent electrical stimulus can be inhibited.

Figure 1:
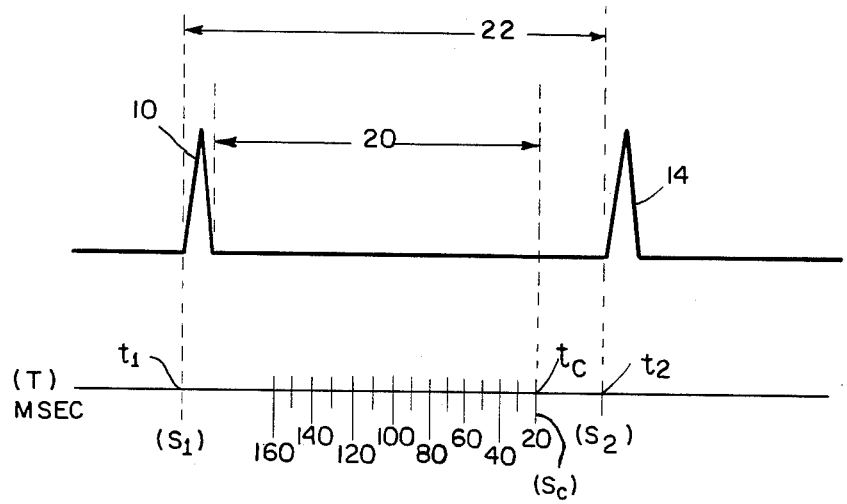
FIG. 1 is a diagrammatic representation of heartbeats propagated by stimuli $S_1$ and $S_2$ and the application of an inhibiting electrical stimuli $S_c$ at various times (T) within the refractory period.

The basis of our invention is best illustrated in FIG. 1. Generally speaking, we have determined that by pacing the heart, arrhythmias such as, for example, tachycardia and fibrillation, can be inhibited. Electrical stimuli $S_1$ and $S_2$, each having a pulse width of approximately 2.0 milliseconds and a threshold current of between 1.0 to 1.4 milliamps, were applied to a human heart at different times $t_1$ and $t_2$ to produce heartbeat responses 10 and 14, respectively. A conditioning electrical stimulus $S_c$ was applied to the heart at time $t_c$ before the stimulated heartbeat 14 and within the refractory period 20 of the heartbeat 10. The refractory period 20 is defined as the period after a heartbeat 10 during which the heart recovers excitability.

It is known that, during the refractory period 20, an electrical stimulus can be applied to the heart which will not propagate a response. The refractory period 20 was determined by applying an electrical stimulus $S_1$ at time $t_1$ to produce heartbeat 10 and an electrical stimulus $S_2$ at a subsequent time $t_2$ to produce heartbeat 14. The time $t_2$ was moved progressively closer to the time $t_1$ until the electrical stimulus $S_2$ did not propagate a response. The longest time interval between times $t_1$ and $t_2$ which did not result in a response on two consecutive applications of the electrical stimulus $S_2$ was defined as the effective refractory period 20.

After determining the effective refractory period 20, the effect of changes in time (T) and in the current (I) for the conditioning electrical stimulus $S_c$ was analyzed. Since arrhythmias can originate within various areas of a heart, the effect of the position of one or more electrodes with respect to various areas of the heart for inhibiting the subsequent heartbeat 14 was also analyzed. These analyses were conducted with respect to inhibition of arrhythmias originating in both the ventricle and atrium of the heart.

Once the effective refractory period 20 was determined, a time interval 22 between times $t_1$ and $t_2$ of approximately 10 to 20 milliseconds greater than the effective refractory period 20 was chosen for application of the electrical stimulus $S_2$ to produce the heartbeat 14. At a time $t_c$ of 20 milliseconds prior to the electrical stimulus $S_2$, a first conditioning electrical stimulus $S_c$ was applied to the heart. The current (I) of the conditioning electrical stimulus $S_c$ was maintained below the threshold current of the electrical stimulus $S_2$ applied at time $t_2$ to produce heartbeat 14. At the first time $t_c$, the current (I) of the conditioning electrical stimulus $S_c$ was increased in 0.1 to 0.3 milliamp increments until the conditioning electrical stimulus $S_c$ inhibited the propagation of heartbeat 14 when the subsequent electrical stimulus $S_2$ was applied at time $t_2$. The conditioning electrical stimulus $S_c$ was applied at 10 millisecond time intervals prior to the time $t_2$ such that the time period between the stimuli $S_c$, $S_2$ increased by 10 millisecond intervals. At each time $t_c$, the current (I) was gradually increased until a response to the subsequent electrical stimulus $S_2$ applied at time $t_2$ was inhibited by the conditioning electrical stimulus $S_C$. This process was repeated until a time interval between the stimuli $S_c$, $S_2$ was obtained at which the current (I) of 10 milliamps did not result in inhibition of the heartbeat 14 propagated by the subsequent electrical stimulus applied $S_2$ at time $t_2$. The pulse width of the conditioning electrical stimuli $S_c$ was approximately 2 milliseconds.

Figure 2:
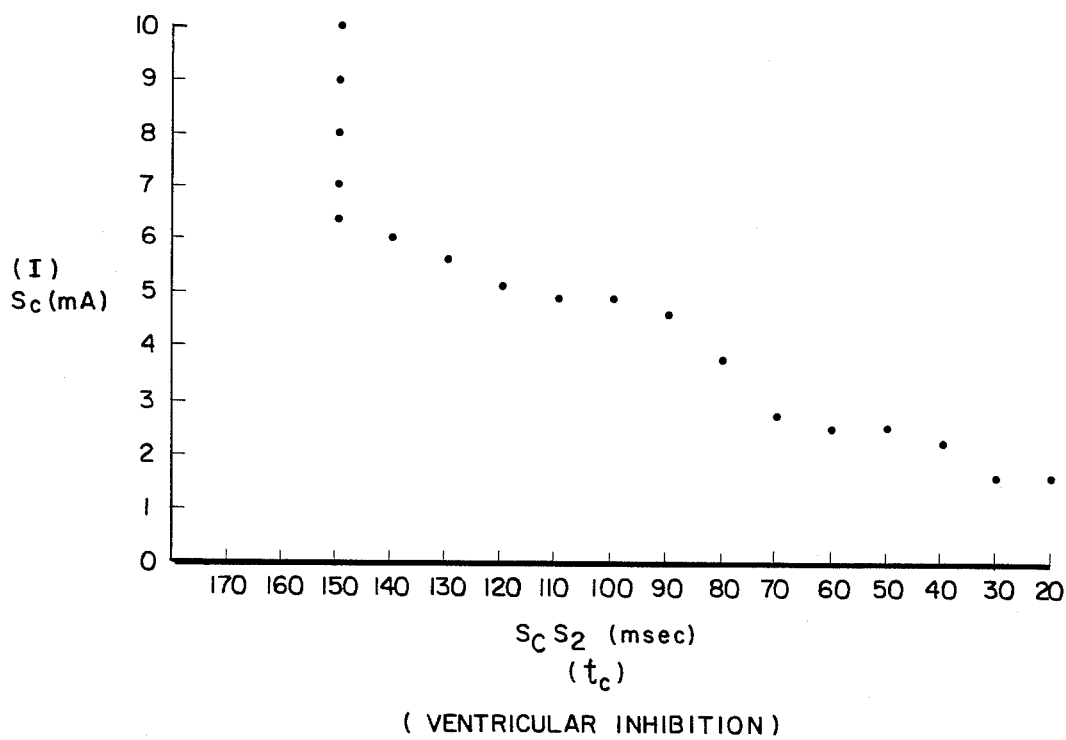
FIG. 2 is a graphical representation of the relationship between the time $t_c$ before the stimulus $S_2$ when the inhibiting electrical stimulus $S_c$ is applied to the ventricle and the current (I) of the inhibiting electrical stimulus $S_c$.

FIG. 2 is a graphical representation of the relationship between the current (I) of the conditioning electrical stimulus $S_c$ and the time period between the time $t_c$ when the conditioning electrical stimulus $S_c$ was applied and the time $t_2$ when the subsequent electrical stimulus $S_2$ was applied. The graphical illustration of FIG. 2 shows the result of inhibition in the heart ventricle. As shown in FIG. 2, the relationship between the current (I) of the conditioning electrical stimuli $S_c$ and the time $t_c$ is generally curvilinear. As the time interval $t_c-t_2$ between the application of the conditioning electrical stimulus $S_c$ and the subsequent electrical stimulus $S_2$ increases, the current (I) of the conditioning electrical stimulus $S_c$ needed to inhibit the heartbeat 14 also increases. Thus, the earlier the conditioning electrical stimulus $S_c$ is applied after heartbeat 10, the greater the current (I) needed to inhibit the heartbeat 14.

Figure 3:
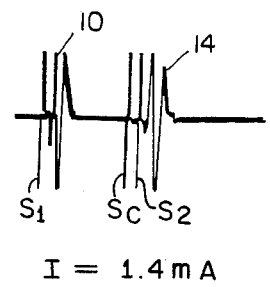
FIG. 3 is an illustration of analog data from a patient demonstrating the relationship shown in FIG. 2.
Figure 3:
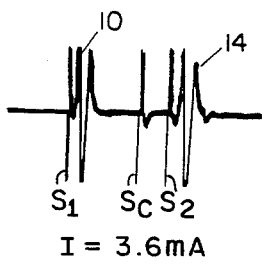
Figure 3:
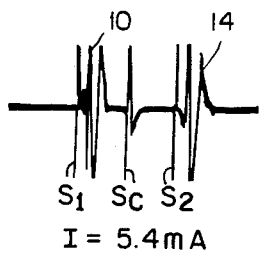
Figure 3:
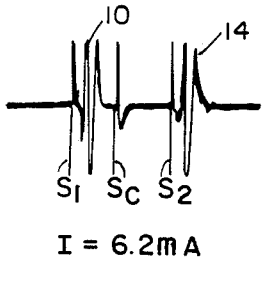
Figure 3:
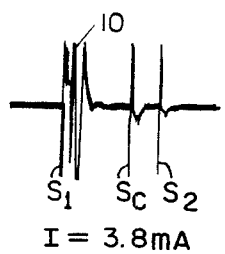
Figure 3:
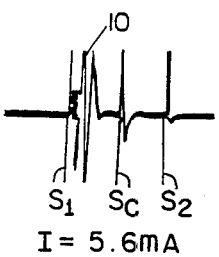
Figure 3:
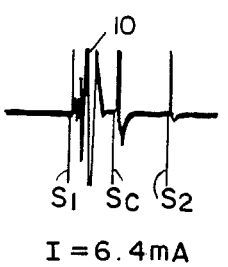

In FIG. 3, analog data from a patient is shown, demonstating the relationship between the current (I) of the conditioning electrical stimulus $S_c$ and the time $t_c$ graphically illustrated in FIG. 2. The time interval 22 ($t_1-t_2$) between stimuli $S_1$ and $S_2$ was 270 milliseconds. The analog data shown at the left of FIG. 3 demonstrates the maximum current (I) of the conditioning electrical stimulus $S_c$ for various times $t_c$ where the conditioning electrical stimulus $S_c$ did not inhibit the heartbeat 14. The right side of FIG. 3 shows the minimum current (I) of the conditioning electrical stimulus $S_c$ which inhibited the response to the electrical stimulus $S_2$ applied at time $t_2$.

As shown in FIGS. 2 and 3, the maximum time $t_c$ between stimuli $S_c$ and $S_2$ at which the conditioning electrical stimulus $S_c$ inhibited the heartbeat 14 was 150 milliseconds. The inhibition at time $t_c$ of 150 milliseconds was achieved at a current (I) of 6.4 milliamps. Thus, approximately two-thirds of the maximum time interval $t_c-t_2$, where the conditioning electrical stimulus $S_c$ would inhibit the heartbeat 14 occurred at currents (I) less than 5.0 milliamps for the conditioning electrical stimuli $S_c$.

Figure 4:
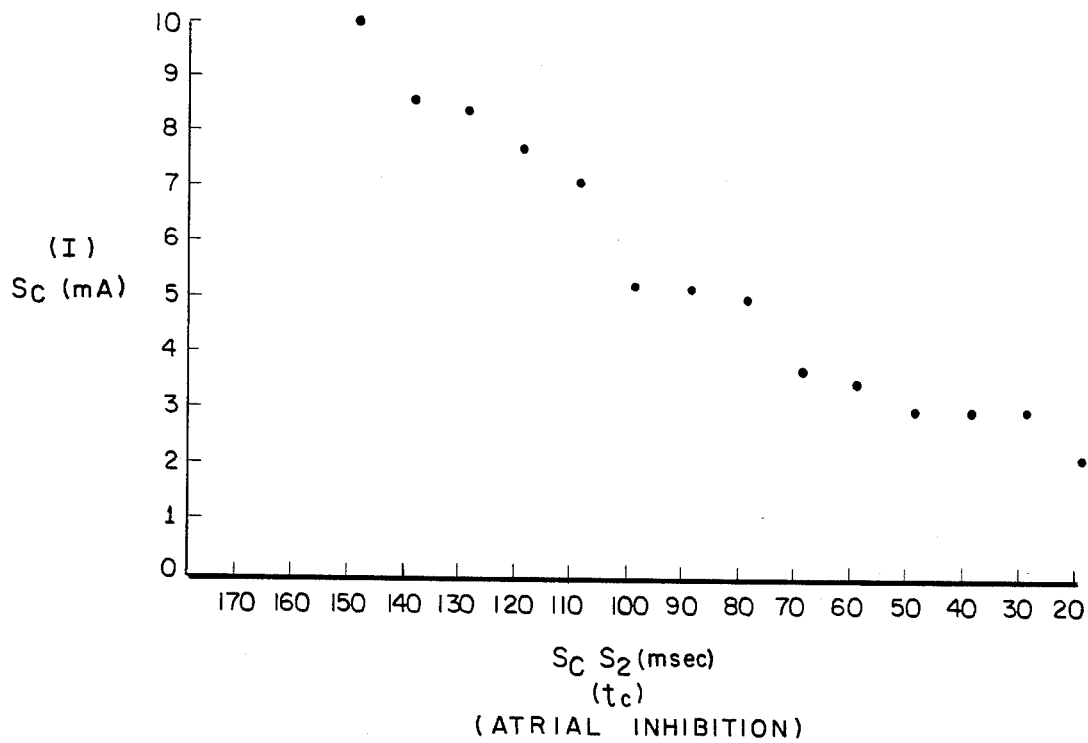
FIG. 4 is a graphical representation of the relationship between the time $t_c$ before the stimulus $S_2$ when the inhibiting electrical stimulus $S_c$ is applied to the atrium and the current (I) of the inhibiting electrical stimulus $S_c$.
Figure 5:
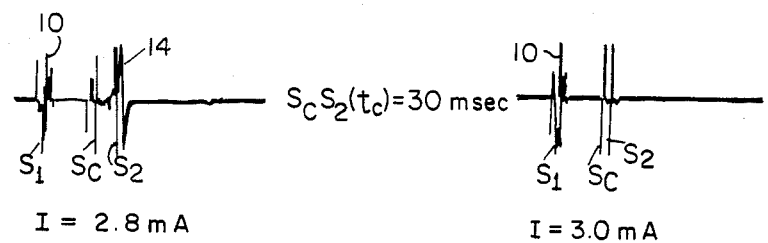
FIG. 5 is an illustration of analog data from a patient demonstrating the relationship shown in FIG. 4.
Figure 5:
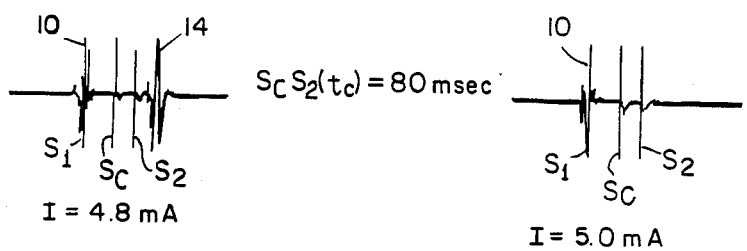
Figure 5:
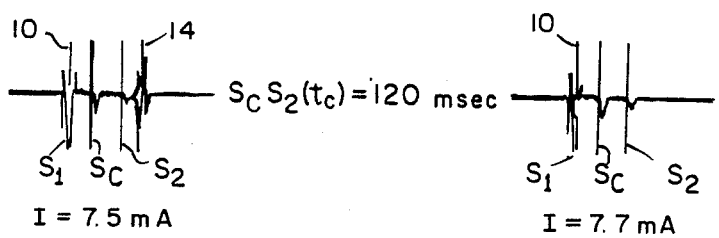
Figure 5:
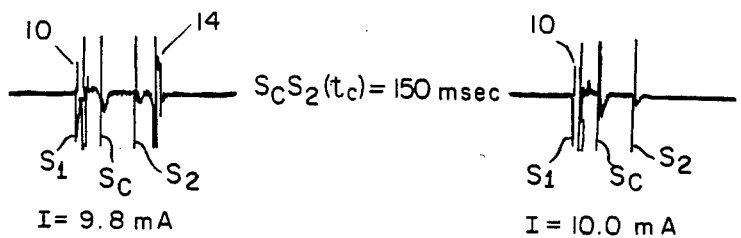

Referring to FIGS. 4 and 5, a similar analysis was conducted to study the effect of inhibition of responses 14 originating in the heart atrium. Again, the relationship between the current (I) of the conditioning electrical stimulus $S_2$ and the time $t_c$ is curvilinear, as particularly shown in FIG. 4. FIG. 5 represents analog data from a patient demonstrating the relationship between current (I) of the conditioning electrical stimulus $S_c$ and the time $t_c$ before the time $t_2$ when the stimulus $S_2$ was applied.

In the analysis of inhibition in the atrium, the time interval 22 ($t_1-t_2$) between the heartbeat 10 and the heartbeat 14 was 240 milliseconds. As shown in FIG. 4, the maximum time $t_c$ before the stimulus $S_2$ at which the conditioning electrical stimulus $S_c$ still inhibited the response to the stimulus $S_2$ was 150 milliseconds. It should be noted that a significant portion of inhibition was obtained above the current (I) of 5.0 milliamps. Thus, unlike the inhibition in the heart ventricle, there is a significant amount of inhibition that occurs in the heart atrium when the current (I) of the conditioning electrical stimulus $S_c$ is greater than 5.0 milliamps.

As with the analog data shown in FIG. 3, the left side of FIG. 5 demonstrates the maximum current (I) of the conditioning electrical stimulus $S_c$ which did not inhibit the heartbeat 14, and the right side of FIG. 4 demonstrates the minimum current (I) of the conditioning electrical stimulus $S_c$ which always produced an inhibition of the heartbeat 14.

In the analysis of the method of our invention, multiple electrode catheters were inserted percutaneously into the femoral and/or brachial veins and positioned at multiple areas of the heart in the atrium or ventricle. For the ventricular inhibition analysis, the electrodes were spaced apart approximately 10 millimeters. For the atrial inhibition analysis, the electrodes were spaced apart approximately 5 millimeters. It was determined that inhibition of the heartbeat 14 propagated by the electrical stimuli $S_2$ applied at time $t_2$ was much more efficient when the conditioning electrical stimulus $S_c$ was applied nearer to the area of the heart where the electrical stimulus $S_2$ propagating heartbeat 14 was applied.

Figure 7:
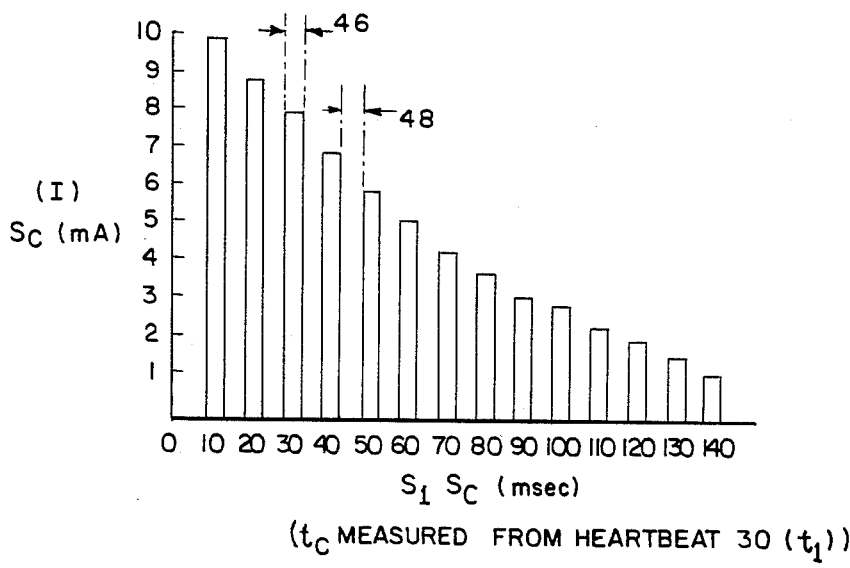
FIG. 7 is a chart showing the relationship between the time $t_c$ after a selected heartbeat 30 and the current (I) of inhibiting electrical stimuli $S_c$ being applied in accordance with the invention to inhibit cardiac arrhythmias.
Figure 6:
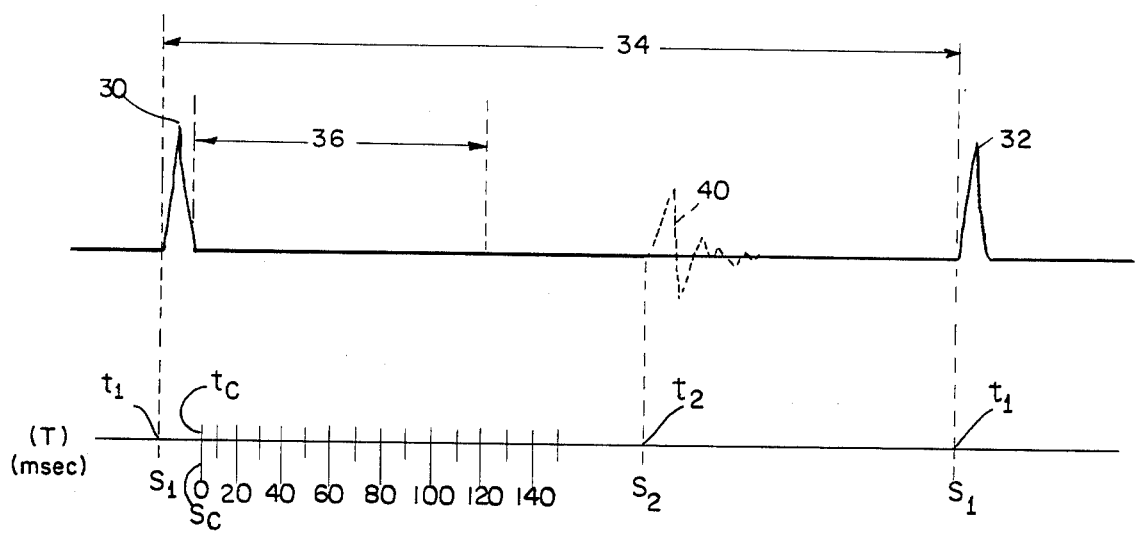
FIG. 6 is a diagrammatic representation of the method according to the present invention of inhibiting cardiac arrhythmias between heartbeats by applying inhibiting electrical stimuli $S_c$ according to the relationships shown in FIGS. 2 and 4.

FIGS. 6 and 7 show the application of the relationships shown in FIGS. 1-5 in our method of inhibiting spontaneous arrhythmic responses in a heart. Referring particularly to FIG. 6, a heart has normal heartbeats 30 and 32 having a time interval 34 ($t_1$–$t_1$) therebetween. Each heartbeat has a refractory period 36. Spontaneous arrhythmias 40, such as tachycardia, fibrillation, or a beat that initiates tachycardia or fibrillation, typically occur between the refractory period 36 of the prior heartbeat 30 and the next normal heartbeat 32. Assuming that the arrhythmic response 40 occurs at a time $t_2$ comparable to a time $t_2$ in FIG. 1, the arrhythmic response 40 can be inhibited by the application of a conditioning electrical stimulus $S_c$ at the appropriate time $t_c$ as long as the conditioning electrical response $S_c$ has a sufficient current (I). Since the time $t_2$ when the spontaneous arrhythmic response 40 will occur is unknown, the conditioning electrical stimulus $S_c$ should be applied very early after the heartbeat 30. By applying a train of conditioning electrical stimuli $S_c$ at various times $t_c$ after the heartbeat 30, a spontaneous arrhythmic response 40 can be inhibited within the time interval between the refractory period 36 and the time $t_1$ when the next normal heartbeat 32 occurs. Furthermore, if arrhythmic response 40 is the trigger that starts the tachycardia or fibrillation, $S_c$ can be used to either prevent the trigger, as described above, or instead of delivering $S_c$ after each beat 30, the spontaneous electrical activity of the heart can be sensed and whenever response 40 occurs and is sensed, $S_c$ can be delivered in the refractory period of response 40 to prevent the subsequent tachycardia or fibrillation precipitated by the trigger 40.

As shown in FIG. 7, the current (I) of the conditioning electrical stimulus $S_c$ can be varied in a curvilinear relationship (similar to FIGS. 2 and 4) with respect to the time $t_c$ when the conditioning electrical stimulus $S_c$ is applied after the heartbeat 30. In FIG. 7, the time $t_c$ is measured from the heartbeat 30 and thus represents the time interval $t_{1\text{-}tc}$ between the stimuli $S_1$ and $S_c$. It is necessary to measure the time $t_c$ from time $t_1$, since the time $t_2$ when the spontaneous response 40 occurs is unknown. As can be seen in FIG. 7, the current (I) of the stimulus $S_c$ varies in an inverse relationship with respect to time $t_c$ when the time $t_c$ is measured from the heartbeat 30 ($t_1$). This would also be true if time $t_c$ is measured from the response 40 triggering tachycardia or fibrillation.

The conditioning electrical stimuli $S_c$ have, for example, a current (I) range of between 0 and 10 milliamps. Further, each conditioning electrical stimulus $S_c$ will have a pulse width 46 of, for example, 1.8 to 2.0 milliseconds. The pulse width 46 may be varied, which in turn, will vary the effective current (I). The frequency 48 with which the conditioning stimuli $S_c$ are applied to the heart may vary, depending upon factors such as electrode size, position of the electrodes, site of arrhythmia development, type of arrhythmia, and the particular heart. It will also be appreciated that these factors may influence the range of current (I) and the pulse width 46 for the conditioning electrical stimuli $S_c$.

Figure 8:
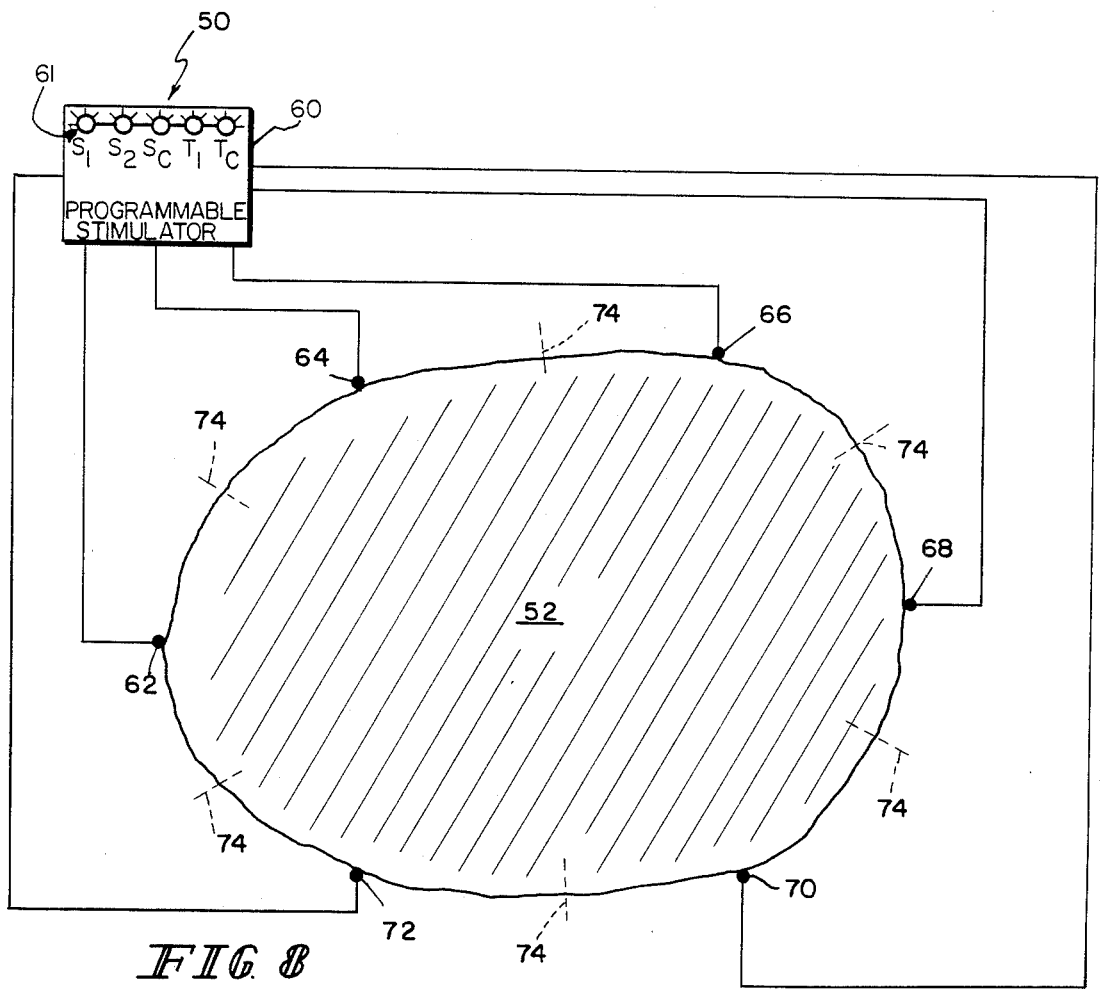
FIG. 8 is a schematic of a pacemaker system embodying the present invention for inhibiting cardiac arrhythmias.

Referring now to FIG. 8, a pacing system 50 embodying the method of the present invention for inhibiting arrhythmic responses in a heart 52 includes a conventional programmable stimulator 60, i.e., pacemaker. A pacemaker 60 which may be used is, for example, a programmable antitachycardia pacemaker. In particular the Symbios series of programmable pacemakers manufactured by Medtronic, Inc., Minneapolis, Minn. may be used. These programmable pacemakers include a sensor for sensing rhythmic and arrhythmic heartbeats, a generator for generating electrical stimuli or pulses and an external programming device for determining th time when the stimuli or pulses are to be generated and applied to the heart, the number and frequency of the electrical pulses, the duration of the electrical pulses and the amplitude of the electrical pulses. The circuitry contained within these conventional pacemakers and the operation of such circuitry is well known to those skilled in the art. The conventional pacemaker 60 may require slight modification to be capable of applying the conditioning electrical stimuli $S_c$ in accordance with the present invention; however, such modifications are within the state of the prior art.

Multiple electrodes 62, 64, 66, 68, 70, and 72 are positioned at various areas of the heart 52. Each electrode is electrically coupled to the stimulator 60. Adjacent pairs of electrodes, such as, for example, 62 and 64, are spaced apart a predetermined distance such that an arrhythmic response originating at a point 74 between the electrodes 62 and 64 will be inhibited. Each conditioning electrical stimulus $S_c$ is applied simultaneously to each of the electrodes 60, 64, 66, 68, 70, and 72. While one method of positioning the electrodes on the heart has previously been described, various other methods of positioning the electrodes may be used without departing from the scope of the present invention.

In the method according to our invention, the user of the pacemaker system 50 determines the time period 34 ($t_1$–$t_1$) between normal heartbeats 30 and 32 and a refractory period 36. One or more times $t_c$ after selected heartbeats 30 are determined for the application of one or more conditioning electrical stimuli $S_c$ to inhibit the occurrence of spontaneous arrhythmic responses 40 at an unknown times $t_2$. It will also be appreciated that the stimuli $S_c$ may be applied at times $t_c$ after responses 40 which trigger tachycardia or fibrillation. The current (I) of each conditioning electrical stimuli $S_c$ is determined as a function of the time $t_c$ when the conditioning stimulus $S_c$ is to be applied to the heart 52. By repeatedly applying the conditioning stimuli $S_c$ after selected heartbeats 30, spontaneous arrhythmic responses 40 or the arrhythmic response propagated by triggers 40 can be inhibited.

While we have described and shown the conditioning stimuli $S_c$ as being applied within the refractory period 36 after a heartbeat 30, the stimuli $S_c$ may be applied after the refractory period 36. If applied after the refractory period 36, the current (I) of the conditioning stimulus $S_c$ must be less than a predetermined threshold current of a stimulus (such as $S_2$ in FIG. 1) which would propagate a response between the refractory period 36 and the next heartbeat 32. However, the current (I) of the conditioning stimulus $S_c$ must be sufficient to inhibit responses 40. Thus, while desirable, our invention is not intended to be limited to application of conditioning stimuli $S_c$ only within the refractory period 36.

What is claimed is:

1. In a method of pacing a heart, which includes the step of applying electrical stimuli to the heart to propagate rhythmic responses, the improvement comprising the steps of determining a characteristic refractory time period between a patient's rhythmic responses within which an electrical stimulus can be applied to the patient's heart without propagating a heart response, sensing each rhythmic heart response, determining a time within the refractory time period after each sensed rhythmic heart response for the application of an electrical stimulus to the heart, after each rhythmic heart response, generating a conditioning electrical stimulus having an amplitude which is a function of the determined time so that it will not propagate a heart response, and applying the conditioning electrical stimulus to the patient's heart at the determined time during the refractory time period after the sensed rhythmic heart response to inhibit a subsequent spontaneous arrhythmic response before the next rhythmic heart response.

2. A method of inhibiting cardiac arrhythmias before they occur comprising the steps of determining a characteristic refractory time period between a patient's heartbeats within which an electrical stimulus can be applied to the patient's heart without propagating a heart response, sensing each beat of the patient's heart; after each sensed heartbeat, generating an electrical pulse having an amplitude which will not propagate a heart response, and applying the electrical pulse to a portion of the patient's heart during the refractory time period after each sensed heartbeat to inhibit a subsequent spontaneous arrhythmic beat before it occurs.

3. The method of claim 2 further comprising the step of, before generating the electrical pulse, determining a time within the refractory time period after each sensed heartbeat when the pulse is to be applied.

4. The method of claim 3 wherein the step of generating the electrical pulse includes generating an electrical pulse having a predetermined duration and an amplitude that is a function of the predetermined duration.

5. The method of claim 3 wherein the step of generating the electrical pulse includes generating an electrical pulse having an amplitude that is a function of the determined time.

6. The method of claim 5 wherein the step of generating the electrical pulse further includes generating an electrical pulse having a predetermined duration and an amplitude that is a function of the predetermined duration.

7. The method of claim 6 wherein the determined time is less than the characteristic refractory time period of the patient's heartbeats.

8. The method of claim 2 comprising the steps of, after each sensed heartbeat, generating a plurality of electrical pulses each having an amplitude and duration that will not propagate a heart response and applying the electrical pulses to portions of the patient's heart during the refractory time period after each heartbeat to inhibit spontaneous arrhythmic beats before they occur.

9. The method of claim 8 comprising the step of, before generating the plurality of electrical pulses, determining a plurality of times during the refractory time period after each sensed heartbeat when the electrical pulses are to be applied.

10. The method of claim 9 wherein the step of generating the plurality of electrical pulses includes generating a plurality of electrical pulses having an amplitude that is a function of the determined time when it is to be applied.

11. The method of claim 2 further comprising the step of disposing a plurality of electrodes at various areas of the heart and applying the electrical pulse to each electrode.

12. The method of claim 11 wherein the step of applying the electrical pulse includes applying the electrical pulse simultaneously to the electrodes.

* * * * *

UNITED STATES PATENT AND TRADEMARK OFFICE
CERTIFICATE OF CORRECTION

PATENT NO. : 4,554,922

DATED : November 26, 1985

INVENTOR(S) : Eric N. Prystowsky and Douglas P. Zipes

It is certified that error appears in the above-identified patent and that said Letters Patent is hereby corrected as shown below:

Column 5, line 39, delete the material between "interval" and "between" and insert therefor
--$t_1 - t_c$--.

Column 5, lines 66-68 through Column 6, lines 1-11, delete in its entirety and insert the following in place thereof:

--Exemplary of available programmable stimulators are the Symbios series of programmable pacemakers manufactured by Medtronic Inc., Minneapolis, Minnesota; the Bloom programmable stimulator systems manufactured by Bloom Associates, Ltd., Reading, Pennsylvania; and the M.E.C.A. stimulators (used with WPI Stimulus Isolators) available from Medical Electronics Consulting Associates, Indianapolis, Indiana. Such programmable stimulators include a sensor for sensing rhythmic and arrhythmic heartbeats, a generator for generating electrical stimuli or pulses and an external programming means 61 for determining the time when the stimuli or pulses are to be generated and applied to the heart, the number and frequency of the electrical pulses, the duration of the electrical pulses and the amplitudes of the electrical pulses. The operation of such programmable stimulators is well known to those skilled in the art.--

UNITED STATES PATENT AND TRADEMARK OFFICE
CERTIFICATE OF CORRECTION

PATENT NO. : 4,554,922  Page 2 of 3

DATED : November 26, 1985

INVENTOR(S) : Eric N. Prystowsky and Douglas P. Zipes

It is certified that error appears in the above-identified patent and that said Letters Patent is hereby corrected as shown below:

Column 7, line 1 (Claim 1), delete "an", and in place thereof insert --at least one conditioning--.

Column 7, line 2 (Claim 1), before "after", insert --and--.

Column 7, line 3 (Claim 1), delete "a", and in place thereof insert --at least one--.

Column 7, line 8 (Claim 1), delete "the" (second occurrence), and in place thereof insert --each--.

Column 7, line 9 (Claim 1), after "to", insert --effectively prolong the refractory period and--.

Column 7, line 9 (Claim 1), delete "a", and in place thereof insert --the propogation of--.

Column 7, line 10 (Claim 1), delete "response" and in place thereof insert --beats by spontaneous stimuli--.

Column 7, line 12 (Claim 2), delete "before".

Column 7, line 13 (Claim 2), delete "they occur".

Column 7, line 15 (Claim 2), before "heartbeats", insert --normal rhythmic--.

Column 7, line 17 (Claim 2), after "each", insert --rhythmic--.

UNITED STATES PATENT AND TRADEMARK OFFICE
CERTIFICATE OF CORRECTION

PATENT NO. : 4,554,922

DATED : November 26, 1985

INVENTOR(S) : Eric N. Prystowsky and Douglas P. Zipes

It is certified that error appears in the above-identified patent and that said Letters Patent is hereby corrected as shown below:

Column 7, line 18 (Claim 2), after "sensed", insert --rhythmic--.

Column 7, line 18 (Claim 2), delete "an" and insert in place thereof --at least one--.

Column 7, line 20 (Claim 2), after "to", insert --at least--.

Column 7, line 22 (Claim 2), after "sensed", insert --rhythmic--.

Column 7, line 22 (Claim 2), after "to", insert --effectively prolong the refractory period and--.

Column 7, line 22 (Claim 2), delete "a", and in place thereof insert --propogation of--.

Column 7, line 23, delete "before it occurs", and in place thereof insert --by spontaneous arrhythmic stimuli--.

Signed and Sealed this

Twenty-ninth Day of July 1986

[SEAL]

Attest:

DONALD J. QUIGG

Attesting Officer  Commissioner of Patents and Trademarks